United States Patent [19]

Cerise et al.

[11] Patent Number: 5,211,948
[45] Date of Patent: May 18, 1993

[54] PROCESS FOR THE PREPARATION OF A POWDERED EXTRACT OF VALERIAN ROOTS

[75] Inventors: Léon Cerise; Peter D. Leathwood, both of Blonay; Tito L. Lunder, Morges, all of Switzerland

[73] Assignee: Nestec S.A., Vevy, Switzerland

[21] Appl. No.: 876,119

[22] Filed: Apr. 29, 1992

Related U.S. Application Data

[63] Continuation of Ser. No. 413,319, Sep. 27, 1989, abandoned.

[30] Foreign Application Priority Data

Oct. 12, 1988 [EP] European Pat. Off. .......... 88116920

[51] Int. Cl.$^5$ ........................ A61K 35/78; A23G 3/30
[52] U.S. Cl. ........................ 424/195.1; 426/3
[58] Field of Search .......................... 424/195.1; 426/3

[56] References Cited

U.S. PATENT DOCUMENTS

| | | | |
|---|---|---|---|
| 3,047,463 | 7/1962 | Merkel | 424/195.1 |
| 3,422,090 | 1/1969 | Thies et al. | |
| 3,869,476 | 3/1975 | Thies et al. | |
| 4,313,930 | 2/1982 | Wischniewski et al. | |
| 4,807,648 | 2/1989 | Breckwoldt | 131/359 |
| 4,960,597 | 10/1990 | Farbood | 426/3 |
| 4,987,150 | 1/1991 | Kuruno | 514/455 |

FOREIGN PATENT DOCUMENTS

| | | |
|---|---|---|
| 2230626 | 6/1972 | Fed. Rep. of Germany ... 424/195.1 |
| 2654709 | 4/1978 | Fed. Rep. of Germany . |
| 1091695 | 11/1967 | United Kingdom . |

OTHER PUBLICATIONS

Steinmetz E. F. Codex Vegetabilis 1957 Amsterdam 1182–1184.
Gstirner F. Chem Abstracts vol. 53 #3485 1959 Pharmacological Testing of Valerian Root.
Prepinsky J. Chem Abstracts vol. 53 #3386 1959 Isolation of Neutral Substances Aleriana.
Duke, James A. CRC Handbook of Medicinal Herbs, CRC Press, Boca Raton, FL 1986 pp. 503–504.
The Merck Index 11th ED Merck & Co. 1989 Rahway NJ p. 1558 #9814.
Leathwood, Aqueous Extract of Valerian Root Improves Sleep Quality in Man. Pharm. Biochem. & Behavior, vol. 17, pp. 65–71, 1982.
H. Braun, "Heilpflanzen-Lexikon Für Ärte und Apotheker," pp. 194–195, Gustau Fischer Verlag, Stuttgart (1974), Translation Provided.

*Primary Examiner*—Michael G. Wityshyn
*Assistant Examiner*—Ralph Gitomer
*Attorney, Agent, or Firm*—Vogt & O'Donnell

[57] ABSTRACT

An aqueous extract of valerian roots is concentrated to concentrate the extract and to eliminate odors which are volatile and which are produced by degradation products of valepotriates. An alcohol or acetone is added to the concentrated valerian extract to precipitate insoluble solids from the concentrated extract. The precipitated solids are separated from the extract, after which the extract is mixed with a carbohydrate and then dried to obtain a powder.

15 Claims, No Drawings

PROCESS FOR THE PREPARATION OF A POWDERED EXTRACT OF VALERIAN ROOTS

CROSS REFERENCE TO RELATED APPLICATION

This application is a continuing application of application Ser. No. 07/413,319, filed Sep. 27, 1989, now abandoned.

BACKGROUND OF THE INVENTION

This invention relates to a process for the preparation of a deodorized powder-form extract of valerian roots.

It is known that the aqueous extract of valerian root has the property of improving sleep in human beings (Pharmacology Biochemistry & Behavior, Vol. 17, pages 65 to 71). These mixtures are taken as infusions and the unpleasant taste and unpleasant odour of these beverages are well known. On the other hand, valerian powder as known at present, when dissolved in water, leads to certain deposits and to a cloudy beverage.

SUMMARY OF THE INVENTION

The object of the present invention is to provide a process for the preparation of a powder-form extract of valerian roots in which an aqueous extract obtained from the valerian roots are deodorized and the substances responsible for the cloudiness of the reconstituted valerian beverage are eliminated.

To deodorize the aqueous valerian root extract, the extract is concentrated to concentrate the extract and to eliminate odors which are volatile and which are produced by degradation products of valepotriates. To eliminate substances responsible for beverage cloudiness, an alcohol or acetone is added to the concentrated extract to form a precipitate of insoluble solids which is separated from the extract by centrifugation.

The invention also relates to a process for the preparation of a powder-form extract of valerian roots in which ground valerian roots are extracted at least once with water, the aqueous extract is concentrated to a dry matter content of 10 to 20%, alcohol or acetone is added to the concentrate to precipitate the gelatinous substances responsible for the cloudy appearance of the beverage reconstituted from the powder, the precipitate is separated from the water-alcohol or water-acetone mixture by centrifugation, a carbohydrate is added as a support for drying to the centrifuged water-alcohol or water-acetone mixture and the resulting mixture is dried to obtain an instant powder.

DESCRIPTION OF EMBODIMENTS OF THE INVENTION

*Valerian* is a perennial herbaceous plant of the genus Valeriana which is found in the temperate regions of North America, Europe and Asia. Among the 170 known species, common valerian (*Valeriana officinalis L.*) is the most widely used for medicinal purposes. However, the process according to the invention is applicable to all species of valerian. Valerian roots are the subterranean part of the valerian plant.

The extraction with water is carried out over a period of 2 to 5 hours at a temperature in the range from 65 to 75° C. The temperature of the water is critical because an excessively high temperature would tend to degrade certain components of the root while an excessively low temperature would not give satisfactory extraction. Three successive extractions with water are preferably carried out. This extraction leads to degradation of the valepotriates while preserving the valerenic acids of the valerian roots.

The aqueous extract is then concentrated to eliminate the unpleasant odors which are volatile and which are produced by degradation products. This concentration step is carried out at a temperature in the range from 30° to 60° C. under a pressure of the order of $2 \times 10^4$ Pa. After about one hour when the odour-producing substances have been removed, the pressure is reduced to approximately $2 \times 10^3$ Pa to complete the elimination of water to a dry matter content of approximately 13 to 17%.

The concentration step is followed by the treatment with alcohol or acetone. The alcohol used is ethanol. Mixing is carried out in such a way that an alcohol or acetone concentration of 48 to 52% is obtained. The mixture is left standing for 8 to 20 hours at ambient temperature so that the insoluble gelatinous compounds precipitate. The precipitate is separated by centrifugation and the remainder of the aqueous extract is mixed with a maltodextrin before drying.

The function of the maltodextrin is to act as a support for the drying process. In addition, it enables a final powder to be obtained which is not too hygroscopic and which has a long shelf life.

Drying is then carried out either *in vacuo* or by spray drying to obtain an instant valerian powder which has retained its sedative character.

If the beverage is reconstituted in water, it is free from deposits and cloudiness, has a neutral taste and no odor. The absence of cloudiness has been demonstrated by nephelometric measures. The valerian powder reconstituted in water gives a maximum optical density peak at approximately 650 nm. In addition, there is no valepotriate in the powder.

In the process according to the invention, the alcohol or acetone enables the compounds responsible for cloudiness to be separated. Another function of the treatment with alcohol is to guarantee an almost sterile process in which the risks of bacterial contamination are minimized.

An extraction yield of 20 to 30% is obtained.

The process according to the invention is carried out in batches or by percolation.

EXAMPLES

The invention is illustrated by the following Examples.

Example 1

A 2000 litre capacity percolator is filled with 250 kg finely ground valerian roots and 1500 kg water preheated to 70° C. A sieve at the bottom of the percolator retains the particles and a heating jacket keeps the temperature at 70° C. during the 4 hours of the first extraction. The extract is continuously recycled from the bottom of the percolator by means of a pump.

The first extract is pumped from the percolator to a reservoir from which it is immediately delivered to a vacuum evaporator having a heating jacket in which water at 48° C. circulates. The volatile substances are eliminated in this evaporator by application of a vacuum of $10^4$ Pa for one hour and, when a dry matter content of 14% has been reached, a vacuum of $2 \times 10^3$ Pa is applied.

94% Alcohol (ethanol) is then added to the concentrated extract so that an ethanol content of 50% is obtained. The mixture is left standing for the precipitate to settle.

A second extraction lasting three hours is carried out in the same percolator with 1000 kg fresh water. A third extraction is carried out in the same percolator for two hours. The second and third extracts are treated in the same way as the first.

At the end of the three extractions, the reservoir contains the total extract containing 50% alcohol. Complete precipitation of the insoluble solids takes one night (12 hours). A centrifuge is used to separate the clear liquid extract from the solids precipitated. The dry matter content of the centrifuged extract is determined to calculate the quantity of maltodextrin to be added to obtain a dilution of 1:1 by weight.

The calculated quantity of maltodextrin is introduced into a vacuum dryer and the clear, concentrated alcoholic extract is added thereto. The alcohol is removed at 50° C. under a reduced pressure progressively reaching $10^3$ Pa.

The final drying step is carried out in the same dryer or, when the extract has acquired the consistency of a syrup, it is dried by spray drying.

A final yield of valerian powder of 23 to 25% is obtained, i.e., approximately 62 kg valerian powder is obtained from 250 kg valerian roots.

Example 2

Example 1 is repeated using acetone instead of ethanol.

The extraction yield obtained is equivalent to that obtained with alcohol.

The difference lies in the fact that the use of the process is more economical.

We claim:

1. A process for treating an aqueous extract of valerian roots comprising concentrating an aqueous extract obtained from valerian roots extracted with water to obtain a concentrated extract having a dry matter content of from 10% to 20% by weight, and to eliminate odors which are volatile and which are produced by degradation products of valepotriates, adding ethanol to the concentrated extract to form an ethanol-containing extract to precipitate insoluble solids therefrom and then centrifuging the ethanol-containing extract to remove precipitated solids therefrom.

2. A process according to claim 1 wherein the ethanol is added to the concentrated extract in an amount to obtain an ethanol concentration of from 48% to 52% by volume.

3. A process according to claim 1 or 2 wherein the aqueous extract is concentrated at a temperature of from 30° C. to 60° C. under a pressure of from $2 \times 10^4$ Pa to $10^3$ Pa.

4. A process according to claim 1 or 2 wherein the aqueous extract is concentrated at a temperature of from 130° C. to 60° C. under a pressure of from $2 \times 10^4$ Pa to $2 \times 10^3$ Pa.

5. A process for treating an extract of valerian roots comprising concentrating an aqueous extract obtained from valerian roots extracted with water to obtain a concentrated extract having a dry matter content of from 10% to 20% by weight, and to eliminate odors which are volatile and which are produced by degradation products of valepotriates, adding acetone to the concentrated extract to form an acetone-containing extract to precipitate insoluble solids therefrom and then centrifuging the acetone-containing concentrated extract to remove precipitated solids therefrom.

6. A process according to claim 5 wherein the acetone is added to the concentrated extract in an amount to obtain an acetone concentration of from 48% to 52% by volume.

7. A process according to claim 5 or 6 wherein the aqueous extract is concentrated at a temperature of from 30° C. to 60° C. under a pressure of from $2 \times 10^4$ Pa to $10^3$ Pa.

8. A process according to claim 5 or 6 wherein the aqueous extract is concentrated at a temperature of from 30° C. to 60° C. under a pressure of from $2 \times 10^4$ Pa to $2 \times 10^3$ Pa.

9. A process for obtaining an extract of valerian roots in powder form comprising:

extracting ground valerian roots with water to obtain an aqueous extract;

concentrating the extract to obtain a concentrated extract having a dry matter content of from 10% to 20% by weight, and to eliminate odors which are volatile and which are produced by degradation products of valepotriates;

adding ethanol to the concentrated extract to form an ethanol-containing extract to precipitate insoluble solids therefrom;

centrifuging the ethanol-containing concentrated extract to remove precipitated solids therefrom;

mixing maltodextrin with the centrifuged extract to provide a support for drying the centrifuged extract; and drying the maltodextrin-supported extract to form a powder.

10. A process according to claim 9 wherein the ground roots are extracted at a temperature of from 65° C. to 75° C., the aqueous extract is concentrated at a temperature of from 30° C. to 60° C. under a pressure of from about $2 \times 10^4$ Pa to about $2 \times 10^3$ Pa and the ethanol is added to the concentrated extract in an amount to obtain an ethanol concentration of from 48% to 52% by volume.

11. A process according to claim 9 wherein the ethanol is added to the concentrated extract in an amount to obtain an ethanol concentration of from 48% to 52% by volume.

12. A process for obtaining an extract of valerian roots in powder form comprising:

extracting ground valerian roots with water to obtain an aqueous extract;

concentrating the extract to obtain a concentrated extract having a dry matter content of from 10% to 20% by weight, and to eliminate odors which are volatile and which are produced by degradation products of valepotriates;

adding acetone to the concentrated extract to form an acetone-containing concentrated extract to precipitate insoluble solids therefrom;

centrifuging the acetone-containing concentrated extract to remove precipitated solids therefrom;

mixing maltodextrin with the centrifuged extract to act as a support for drying the centrifuged extract; and drying the maltodextrin-supported extract to form a powder.

13. A process according to claim 12 wherein the ground roots are extracted at a temperature of from 65° C to 75° C. and the aqueous extract is concentrated at a temperature of from 30° C. to 60° C. under a pressure of from about $2\times10^4$ Pa to about $2\times10^3$ Pa and the acetone is added to the concentrated extract in an amount to obtain an acetone concentration of from 48% to 52% by volume.

14. A process according to claim 12 wherein the acetone is added to the concentrated extract in an amount to obtain an acetone concentration of from 48% to 52% by volume.

15. A process according to claim 1 or 5 or 9 or 12 wherein the extract is concentrated with a vacuum evaporator.

* * * * *